(12) United States Patent
Absil et al.

(10) Patent No.: US 9,039,907 B2
(45) Date of Patent: May 26, 2015

(54) METHODS FOR IMPROVING INTEGRATED PHOTONIC DEVICE UNIFORMITY

(75) Inventors: Philippe Absil, Loupoigne (BE); Shankar Kumar Selvaraja, Ghent (BE)

(73) Assignees: IMEC, Leuven (BE); Universiteit Gent, Ghent (BE)

( * ) Notice: Subject to any disclaimer, the term of this patent is extended or adjusted under 35 U.S.C. 154(b) by 87 days.

(21) Appl. No.: 13/552,506

(22) Filed: Jul. 18, 2012

(65) Prior Publication Data

US 2013/0023067 A1 Jan. 24, 2013

Related U.S. Application Data

(60) Provisional application No. 61/510,047, filed on Jul. 20, 2011.

(51) Int. Cl.
| | | |
|---|---|---|
| *G01L 21/30* | (2006.01) | |
| *G01N 21/95* | (2006.01) | |
| *H01L 21/66* | (2006.01) | |

(52) U.S. Cl.
CPC ............ *G01N 21/9501* (2013.01); *H01L 22/12* (2013.01); *H01L 22/20* (2013.01); *G01B 2210/56* (2013.01)

(58) Field of Classification Search
USPC ...................... 216/59; 438/9; 427/8
See application file for complete search history.

(56) References Cited

U.S. PATENT DOCUMENTS

| | | |
|---|---|---|
| 6,537,606 B2 | 3/2003 | Allen et al. |
| 7,626,183 B2 | 12/2009 | Wagner et al. |
| 2002/0027657 A1* | 3/2002 | Mikkelsen et al. ........... 356/369 |
| 2005/0196114 A1* | 9/2005 | Xu et al. ....................... 385/123 |
| 2007/0292075 A1* | 12/2007 | Montgomery et al. ......... 385/14 |
| 2008/0237492 A1 | 10/2008 | Caliendo et al. |
| 2009/0037015 A1* | 2/2009 | Hofmeester et al. .......... 700/110 |

FOREIGN PATENT DOCUMENTS

| | | |
|---|---|---|
| WO | WO02/14915 A2 | 2/2002 |
| WO | WO2007/143501 A2 | 12/2007 |

OTHER PUBLICATIONS

Krishnamoorthy et al, (Computer Systems Based on Silicon Photonic Interconnects), Jul. 2009, IEEE, vol. 97 Proceedings of the IEEE, p. 1337-1361.*

Dumon et al, (Low-Loss SOI Photonic Wires and Ring Resonators Fabricated With Deep UV Lithography), May 2004, IEEE, vol. 16 No. 5, IEEE Photnics Technology Letters, p. 1328-1330.*

(Continued)

*Primary Examiner* — Binh X Tran
*Assistant Examiner* — David Cathey, Jr.
(74) *Attorney, Agent, or Firm* — McDonnell Boehnen Hulbert & Berghoff LLP (57) ABSTRACT

A method is described for improving the uniformity over a predetermined substrate area of a spectral response of photonic devices fabricated in a thin device layer. The method includes (i) establishing an initial device layer thickness map for the predetermined area, (ii) establishing a linewidth map for the predetermined area, and (iii) establishing an etch depth map for the predetermined area. The method further includes, based on the initial device layer thickness map, the linewidth map and the etch depth map, calculating an optimal device layer thickness map and a corresponding thickness correction map for the predetermined substrate area taking into account photonic device design data. Still further, the method includes performing a location specific corrective etch process in accordance with the thickness correction map.

8 Claims, 4 Drawing Sheets

(56) References Cited

OTHER PUBLICATIONS

Selvaraja et al, (Fabrication of Uniform Photonic Devices Using 193nm Optical Lithography in Silicon-on-Insulator), Jun. 2008, EICO, EICO '08 Eindhaven, p. 359-362.*

Barwicz et al, (Fabrication of Add-Drop Filters Based on Frequency-Matched Microring Resonators), May 2006, IEEE, Journal of Light wave Technology, vol. 24, No. 5, p. 2207-2218.*

European Search Report, European Patent Application No. 12177230.5 dated Dec. 17, 2012.

Toyoda, Noriaki et al., "Gas Cluster Ion Beam Equipment and Applications for Surface Processing", IEEE Transactions on Plasma Science, vol. 36, No. 4, Aug. 2008, pp. 1471-1488.

Allen, L. P. et al., "SOI Uniformity and Surface Smoothness Improvement Using GCIB Processing", 2002 IEEE International SOI Conference, Oct. 2, 2002, pp. 192-193.

* cited by examiner

METHODS FOR IMPROVING INTEGRATED PHOTONIC DEVICE UNIFORMITY

CROSS-REFERENCE TO RELATED APPLICATIONS

This application claims priority under 35 U.S.C. §119(e) to U.S. Provisional Patent Application Ser. No. 61/510,047, filed on Jul. 20, 2011, and entitled "Methods for Improving Integrated Photonic Device Uniformity", the full disclosure of which is incorporated herein by reference.

FIELD

This disclosure relates to methods for improving the uniformity and repeatability of the spectral response of integrated photonic devices.

BACKGROUND

Figure 1:
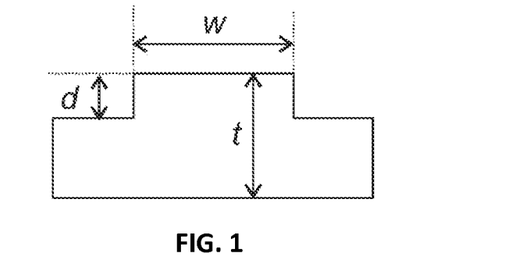
FIG. 1 shows a cross section of an example photonic structure, illustrating thickness t, linewidth w and etch depth d.

Integrated photonic devices fabricated in a high refractive index contrast material system such as, for example, a $Si/SiO_2$ material system are very sensitive to small variations in the device dimensions. Such devices are very sensitive to small variations in the thickness t and etch depth d, as well as to small variations in the linewidth w of the device structures made in the core material (e.g., Si) of the material system. FIG. 1 shows a cross section of an example photonic structure, illustrating thickness t, linewidth w and etch depth d. For example, a variation of 1 nanometer (nm) in the linewidth w can result in a shift in spectral response of wavelength selective photonic devices (such as e.g. ring resonators) on the order of 1 nm or 2 nm. Variations in the linewidth w and etch depth d of device structures may be mainly influenced by the patterning process, including photolithography and etching. Variations in the thickness t or height of the device structures may be determined by the substrate manufacturing process.

For example, integrated photonic devices can be fabricated in thin silicon-on-insulator (SOI) substrates (comprising e.g. a 220 nm thick silicon device layer on top of a 2000 nm thick silicon dioxide layer). The thickness variation of the silicon device layer of a silicon-on-insulator substrate may depend on the vendor specification. The thickness variation is typically 10% over the wafer or substrate. For a 220 nm thick silicon device layer, this means a variation of about 22 nm in thickness of the silicon device layer over the substrate. This may correspond to a shift or variation of about 22 nm to 44 nm in the spectral response of wavelength selective optical devices over the wafer. This shift or variation is unacceptable for commercial viable silicon photonic technology.

In U.S. Pat. No. 6,537,606, a method is described for improving the thickness uniformity and reducing the surface roughness of thin films such as the top silicon film of a silicon-on-insulator wafer. The method uses a vacuum GCIB (Gas Cluster Ion Beam) etching and smoothing process. After initial thickness non-uniformity characterization of the top silicon layer, the film thickness map information is fed into the GCIB beam-control apparatus as a data file. Based on a previously measured beam removal function and a previously measured relationship between etch rate and dose for a particular set of GCIB parameters, a mathematical algorithm is used to create a beam-dose contour to selectively remove surface material and thereby achieve a uniform film thickness.

Overview

Example embodiments of the present disclosure provide methods for improving the uniformity of the spectral response of photonic devices over a wafer or substrate and for improving the repeatability of the spectral response of photonic devices from wafer to wafer and from batch to batch. The methods according to the present disclosure can in particular advantageously be used for integrated photonic devices fabricated in a high refractive index contrast material system.

Particular aspects of the disclosure are set out in the accompanying independent and dependent claims. Features from the dependent claims may be combined with features of the independent claims as appropriate and not merely as explicitly set out in the claims.

The present disclosure provides a method for improving the uniformity and repeatability of the spectral response of photonic devices fabricated in a thin device layer such as a silicon device layer of an SOI substrate, over a predetermined substrate area. In an example, the method comprises: (i) establishing an initial device layer thickness map for the predetermined area; (ii) establishing a linewidth map for the predetermined area; (iii) establishing an etch depth map for the predetermined area; (iv) based on the initial device layer thickness map, the linewidth map and the etch depth map, calculating an optimal device layer thickness map and a corresponding thickness correction map for the predetermined substrate area taking into account device design data; and (v) performing a location specific corrective etch process in accordance with the thickness correction map.

In an example method according to the present disclosure, establishing an initial device layer thickness map comprises measuring the initial thickness of the device layer over the predetermined substrate area as a function of x and y, where x and y are the spatial wafer coordinates. For example, the initial device layer thickness can be measured by means of spectroscopic ellipsometry, e.g. with an accuracy better than 1 nm. In an example, the number of measurement points per wafer can for example be on the order of 300 to 400 points for a 200 mm wafer. However, the present disclosure is not limited thereto, and the number of measurement points per unit area can be higher or lower.

In an example method according to the present disclosure, establishing a linewidth map and establishing an etch depth map may comprise measuring the linewidth and etch depth over the predetermined substrate area as a function of x and y, where x and y are the spatial wafer coordinates. Measuring the linewidth and etch depth may, for example, be done by means of scatterometry.

In an example method according to the present disclosure, calculating an optimum device layer thickness map may comprise calculating as a function of the spatial wafer coordinates an optimum device layer thickness needed for matching a predetermined spectral response of a photonic device. The thickness correction map may be determined by calculating the difference between the optimum device layer thickness and the initial device layer thickness as a function of the spatial wafer coordinates. This difference corresponds to the thickness correction to be performed by the location specific corrective etch process.

In example embodiments of the present disclosure, the location specific corrective etch process may for example be a Gas Cluster Ion Beam process, as for example described in U.S. Pat. No. 6,537,606.

The method of the present disclosure may be particularly relevant and advantageous for integrated photonic devices fabricated in a high refractive index contrast material system, i.e. a material system having a high refractive index contrast between a waveguide core material and a cladding material (difference in refractive index between the core material and the cladding material larger than 1). Photonic devices fabricated in such material systems are highly sensitive to process variations. Examples of such high refractive index contrast material systems are $Si/SiO_2$, $SiN/SiO_2$, $SiON/SiO_2$, $TaO_2/SiO_2$, $Si(O)C/SiO_2$, $InGaAsP/SiO_2$ and $Ge/Al_2O_3$. Other examples are possible as well.

In a first aspect of the present disclosure, the thickness correction map may be established before starting the fabrication of photonic device structures, and the location specific corrective etch process is performed before fabrication of the photonic device structures. Establishing the initial device layer thickness map may comprise measuring the initial thickness of the device layer on the non-processed substrate as a function of the spatial wafer coordinates in the predetermined area. Establishing a linewidth map and establishing an etch depth map may comprise estimating the linewidth and etch depth as a function of the spatial wafer coordinates in the predetermined area, based on data previously collected from process control.

In a second aspect of the present disclosure, the thickness correction map may be established after fabricating the photonic device structures. Establishing the initial device layer thickness map may comprise measuring the thickness of the device layer on the processed substrate as a function of the spatial wafer coordinates in the predetermined area. Establishing a linewidth map and establishing an etch depth map may comprise measuring the linewidth and etch depth as a function of the spatial wafer coordinates in the predetermined area after fabrication of the photonic devices. In this second aspect, additionally the optical response of the photonic devices can be measured and this optical response (such as bandwidth, maximum wavelength, resonance wavelength, and other optical responses) of the devices can be used as an additional input for calculating the thickness correction map.

In example embodiments of the present disclosure a thickness correction can be performed before fabricating the photonic device structures, according to the first aspect. In addition, after fabrication of the photonic device structures a thickness correction may be performed according to the second aspect.

For purposes of summarizing the disclosure and the advantages achieved over the prior art, certain objects and advantages of the disclosure have been described herein above. Of course, it is to be understood that not necessarily all such objects or advantages may be achieved in accordance with any particular embodiment of the disclosure. Thus, for example, those skilled in the art will recognize that embodiments of the present disclosure may be embodied or carried out in a manner that achieves or optimizes one advantage or group of advantages as taught herein without necessarily achieving other objects or advantages as may be taught or suggested herein. Further, it is understood that this overview is merely an example and is not intended to limit the scope of the invention as claimed. The invention as recited in the claims, both as to organization and method of operation, together with features and advantages thereof, may best be understood by reference to the following detailed description when read in conjunction with the accompanying drawings.

BRIEF DESCRIPTION OF THE DRAWINGS

Various exemplary embodiments are described herein with reference to the following drawings, wherein like numerals denote like entities. The drawings described are schematic and are non-limiting. Further, any reference signs in the claims shall not be construed as limiting the scope of the present disclosure. Still further, in the different drawings, the same reference signs refer to the same or analogous elements

DETAILED DESCRIPTION

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure. While the present disclosure will be described with respect to particular example embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the elements listed thereafter; the term "comprising" does not exclude other elements or steps. It is thus to be interpreted as specifying the presence of the stated elements, features, integers, steps or components as referred to, but does not preclude the presence or addition of one or more other elements, features, integers, steps or components, or groups thereof. Thus, the scope of the expression "a device comprising means A and B" should not be limited to devices consisting only of components A and B.

The present disclosure provides methods for improving the uniformity, the repeatability and the controllability of the spectral response of integrated photonic devices, using a location specific corrective etch process, such as a GCIB-based thickness correction process. It is an advantage of methods according to the present disclosure that they result in a better or improved uniformity of the spectral response of photonic devices within a wafer, from wafer to wafer and from batch to batch, as compared to prior art methods.

The non-uniformity of the spectral response of integrated photonic devices depends on three physical factors: linewidth, thickness or height, and refractive index. Since the refractive index of the device layer such as a silicon layer is uniform over a wafer, linewidth and height variation are the dominant sources of non-uniformities. Since these two factors are interlinked, a variation in one factor can be compensated by a variation in the other factor. For example, a variation in height can be compensated by a variation in linewidth or vice-versa, a variation in linewidth can be compensated by a variation in height or thickness.

In a method according to the present disclosure, the thickness of the device(s) is corrected by using a location specific corrective etch process such as a Gas Cluster Ion Beam Process (GCIB), taking into account local linewidth and height data. A tailor-made thickness profile is used that compensates for the other systematic within-wafer process variations, e.g. related to photolithography processes (e.g., mask quality, resist thickness, projection optics, etc.) or related to etch processes (e.g., such as plasma non-uniformities during dry etching).

Figure 2:
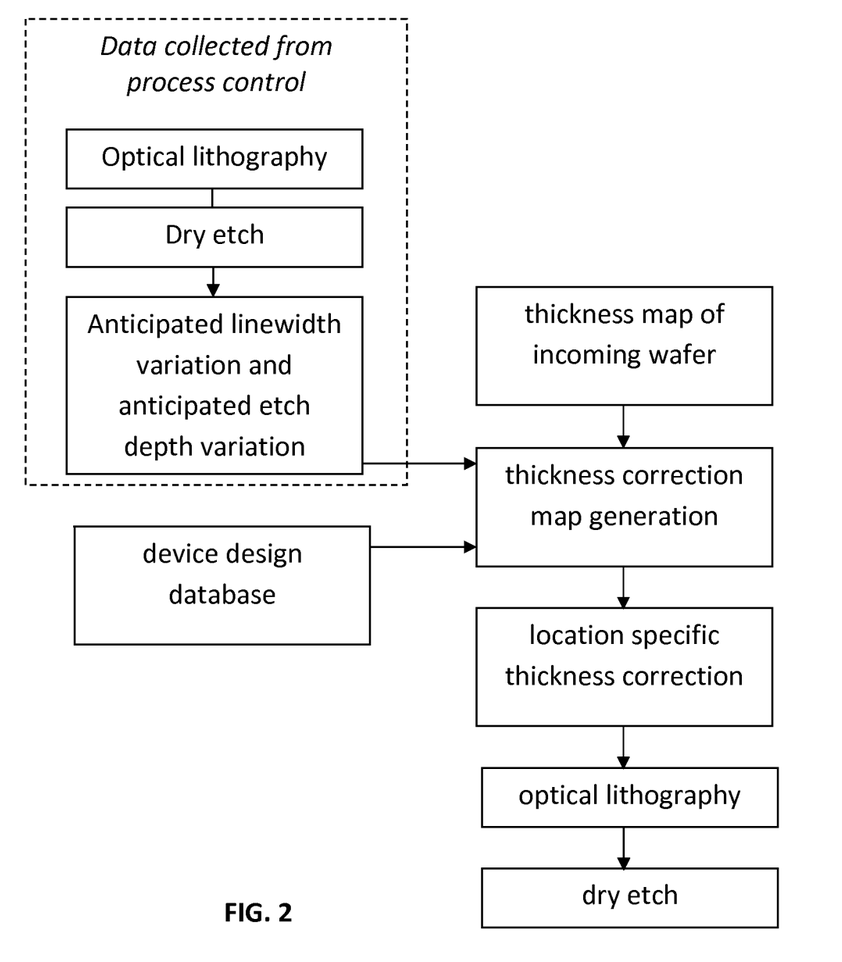
FIG. 2 schematically illustrates an example method according to the present disclosure, wherein a thickness correction is performed before photonic device fabrication.

In a first example aspect, a pre-pattern thickness correction of the device layer (e.g., of a SOI substrate) is performed, i.e. a thickness correction is done before fabrication of the photonic devices. This is schematically illustrated in FIG. 2. A location specific thickness correction is performed based on a thickness correction map. In contrast to prior-art methods, where the thickness correction map is based only on the thickness map of the incoming wafer, in a method according to the present disclosure additional data are taken into account. These additional data may comprise linewidth data and etch depth data previously collected from optical lithography and dry etch process control and device design data.

Based on known process control data from optical lithography and from dry etching, the local linewidth variation and the local etch depth variation may be anticipated or estimated as a function of the spatial wafer coordinates, leading to an anticipated or estimated linewidth map and an anticipated or estimated etch depth map. By combining the initial silicon thickness map, the anticipated linewidth map, the anticipated ethic depth map and design data, a thickness correction map may be generated. This thickness correction map may be calculated based on the local device layer thickness needed for obtaining a predetermined spectral response of the photonic devices to be processed. A location specific thickness correction may be performed in accordance with the thickness correction map. In contrast to prior art methods, this location specific thickness correction may not result in a device layer thickness that is as uniform as possible, but it results in a device layer thickness that is tuned for obtaining optimal device performance. After the location specific thickness correction, the photonic devices may be processed, using e.g. optical lithography steps and dry etching steps. This beneficially leads to devices with uniform spectral response over the wafer.

Figure 3:
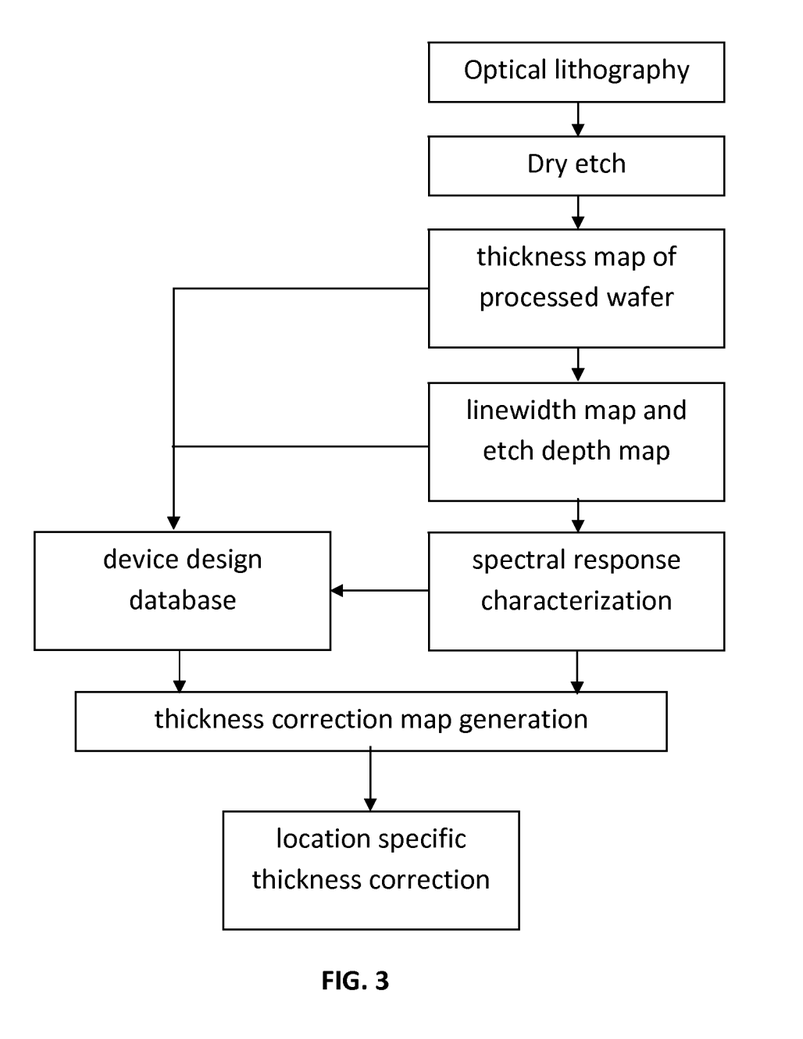
FIG. 3 schematically illustrates an example method according to the present disclosure, wherein a thickness correction is performed after photonic device fabrication.

In a second example aspect, a post-pattern thickness correction of the device layer (e.g., of a SOI substrate) is performed, i.e. a thickness correction is done after fabrication of the photonic devices. This example is schematically illustrated in FIG. 3. After fabrication of the photonic devices using optical lithography and dry etching, a characterization of the local linewidth, etch depth and thickness of the fabricated structures may be performed as a function of the spatial wafer coordinates. In addition to the characterization of linewidth, etch depth and thickness, the spectral response of the photonic devices can be measured. Based on a combination of local thickness, local linewidth, local etch depth, optical response and device design data, a thickness correction map may be generated. This thickness correction map may then be used to perform a location specific thickness correction.

When using GCIB for corrective etching, the ion beam may damage a surface portion of the silicon layer, extending about 10 nm to 20 nm from the silicon surface. The nature of this damage is twofold, firstly structural damage and secondly chemical damage. In the photonic devices, these damages may lead to absorption and scattering of propagating light, resulting in undesirable propagation losses. In order to cure these defects, a thermal annealing step can be performed. The thermal annealing step may preferably be performed at a temperature above 600° C., e.g. at a temperature in the range between 800° C. and 1000° C., during 10 to 30 minutes. For higher annealing temperatures shorter annealing times can be used. It was shown that such thermal annealing step can reduce propagation losses by a factor of 10 and or more.

In example embodiments of the present disclosure, the initial thickness of the device layer, e.g. silicon layer, can be increased by epitaxial growth before performing the location specific thickness correction according to the present disclosure, for example when the minimum initial thickness of the device layer is smaller than an optimum thickness of the device layer. This example is schematically illustrated in FIG. 4, where the device layer is assumed to be a silicon layer, e.g. a top layer of a silicon-on-insulator substrate.

Figure 4:
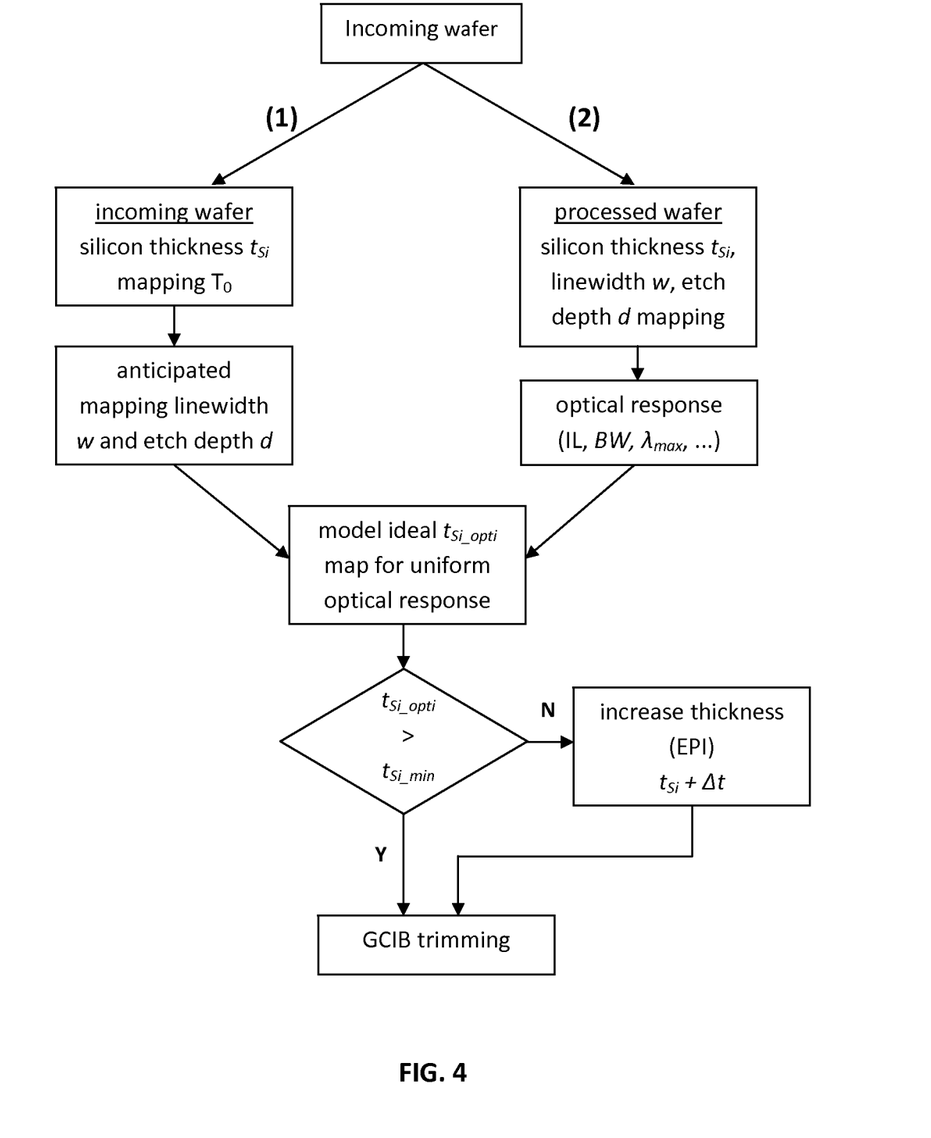
FIG. 4 schematically illustrates example methods according to the present disclosure, wherein the silicon device layer is thickened by epitaxial growth.

FIG. 4 schematically shows a diagram illustrating an example method of the present disclosure. In a first aspect ((1) in FIG. 4), an initial silicon thickness map of an incoming wafer is first established. The silicon layer thickness $t_{Si}$ can be described as a distribution $\delta(x,y,T)$ where x and y are the spatial wafer coordinates and where T is the time. The initial thickness map corresponds to $T=T_0$. Taking into account an anticipated map of linewidth w and etch depth d, and taking into account design data, an optimum silicon thickness $t_{Si\_opti}$ for obtaining a predetermined spectral response may be determined as a function of the spatial wafer coordinates x and y. If the optimum silicon thickness $t_{Si\_opt}$ for the photonic devices to be fabricated is smaller than the minimum initial thickness $t_{Si\_min}$ of the silicon layer, the silicon thickness can be increased by growth of an epitaxial silicon layer with thickness $\Delta t$, and the location specific thickness correction (e.g., by a GCIB process) according to the present disclosure can be performed on the thickened wafer. If the optimum silicon thickness $t_{Si\_opti}$ is larger than the minimum initial thickness $t_{Si\_min}$ over the entire wafer, the method according to the present disclosure can be performed on the incoming wafer, without thickening by epitaxial growth.

In a second aspect ((2) in FIG. 4), the wafer is processed first and a map of silicon thickness $t_{Si}$, linewidth w and etch depth d is established as a function of the spatial wafer coordinates x and y. The optical response of the photonic devices may then be determined (e.g., insertion loss IL, bandwidth BW, $\lambda_{max}$, and so forth), and a map of optimum silicon thickness $t_{Si\_opti}$ may be determined for optimized optical response. The difference between the initial silicon layer thickness $t_{Si}$ and the optimum silicon layer thickness $t_{Si\_opti}$ corresponds to the amount of silicon that needs to be etched locally during the corrective etch process. If the optimum silicon thickness $t_{Si\_opt}$ is smaller than the minimum initial thickness $t_{Si\_min}$ of the silicon layer, the silicon thickness can be increased by growth of an epitaxial silicon layer with thickness $\Delta t$, and the location specific thickness correction (e.g., by a GCIB process) according to the present disclosure can be performed on the thickened wafer. If the optimum silicon thickness $t_{Si\_opti}$ is larger than the minimum initial thickness $t_{Si\_min}$ over the entire wafer, the method according to the present disclosure can be performed on the incoming wafer, without thickening by epitaxial growth.

Simulations were performed to illustrate the use of a method according to the present disclosure for the case of fiber couplers fabricated in a silicon device layer of an SOI wafer. A key parameter for fiber grating couplers is the wavelength $\lambda_{max}$ at which maximum coupling is achieved between a fiber and an integrated waveguide on the substrate. Analysis of the modeling of fiber grating couplers demonstrates that a good approximation of this wavelength of maximum coupling may be given by a linear fit:

$$\lambda_{max} = \lambda_0 + a * t_{Si} + b * w + c * d$$

where a, b and c are fitting parameters.

For a given selection of $\lambda_{max}$ it can be derived that:

$$t_{Si}(x, y, T) = \frac{(\lambda_{max} - \lambda_0 - c * d(x, y, T) - b * w(x, y, T))}{a}$$

Assuming that $T-T_0$ is much smaller than the process stability time scale, this can be written as:

$$t_{Si}(x, y, T) = \frac{(\lambda_{max} - \lambda_0 - c * d(x, y, T_0) - b * w(x, y, T_0))}{a}$$

For a fixed choice of coupling angle (13 degrees), cladding layer thickness (1 micrometer) and grating period (340 nm), a fit over more than 5000 simulation data points results in:

$$\lambda_{max} \cong 1300.9 + 1931.8 * t_{Si} - 205.2 * w - 1151.1 * d$$

wherein $\lambda_{max}$, $t_{Si}$, w and d are expressed in nm.

Based on in-line measurement data, it was found that the average value of $\lambda_{max}$ is 1567 nm with a standard deviation of 3.9 nm wafer-to-wafer within a lot. Based on long term lot-to-lot repeatability measurements, it was found that the average $\lambda_{max}$ can vary from 1552 nm up to 1578 nm, which is a difference of up to 26 nm.

Assuming a GCIB control standard deviation of ±1 nm, the wafer-to-wafer non-uniformity equals the lot-to-lot non-uniformity for $\lambda_{max} = \lambda_{target} \pm 2$ nm (2 nm standard deviation) with a range of about 10 nm, to be compared to the 26 nm without GCIB correction.

Figure 5:
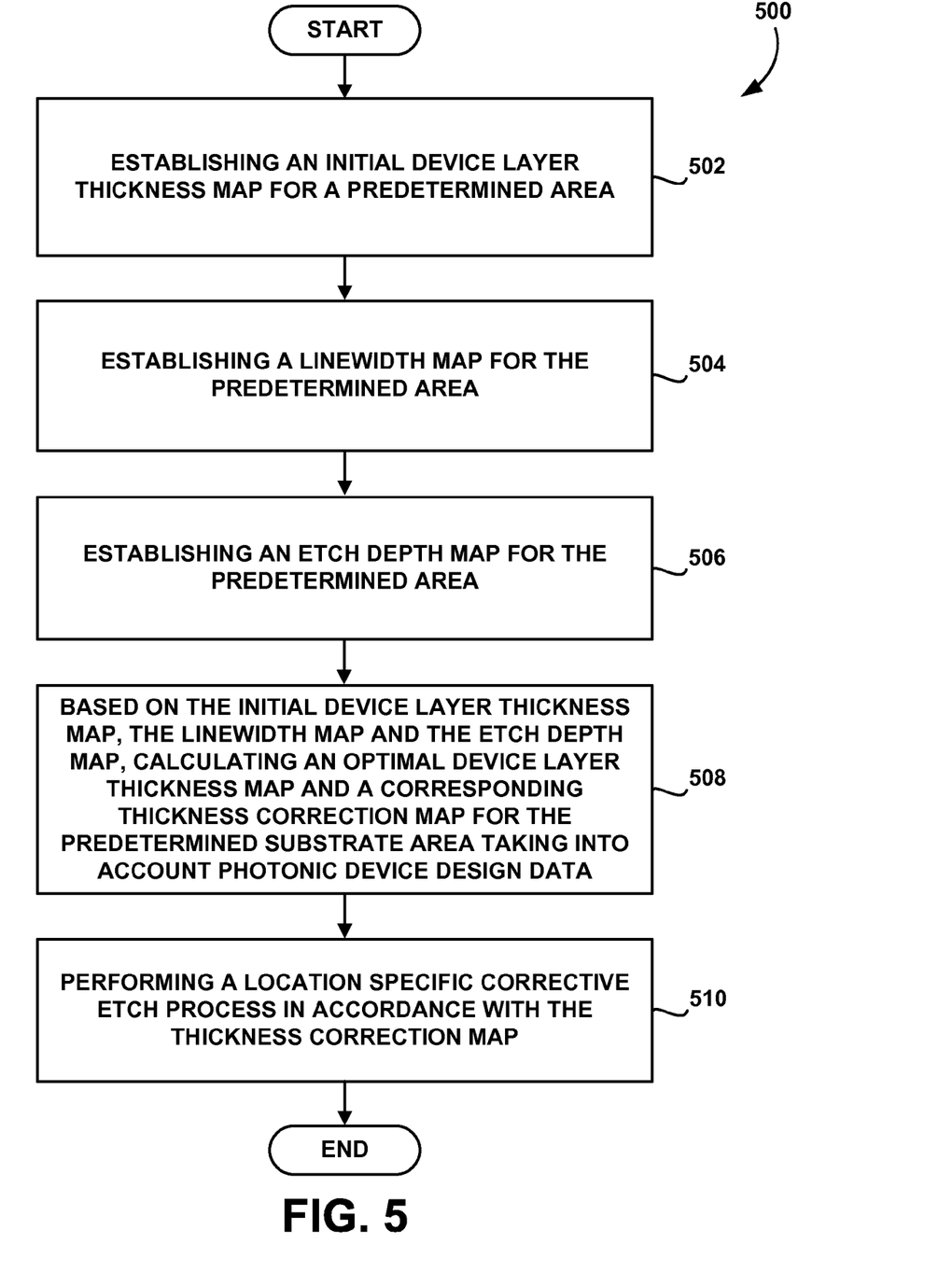
FIG. 5 illustrates a method in accordance with an example of the present disclosure.

An example method 500 in accordance with the present disclosure is depicted in FIG. 5. The method 500 includes, at step 502, establishing an initial device layer thickness map for the predetermined area. Further, the method 500 includes, at step 504, establishing a linewidth map for the predetermined area and, at step 506, establishing an etch depth map for the predetermined area. Still further, the method 500 includes, at step 508, based on (a) the initial device layer thickness map, (b) the linewidth map and (c) the etch depth map, calculating an optimal device layer thickness map and a corresponding thickness correction map for the predetermined substrate area, taking into account photonic device design data. Yet still further, the method 500 includes, at step 510, performing a location specific corrective etch process in accordance with the thickness correction map.

In another example of the present disclosure, a system for improving the uniformity over a predetermined substrate area of a spectral response of photonic devices fabricated in a thin device layer may be provided. The system may be configured to (i) establish an initial device layer thickness map for the predetermined area, (ii) establish a linewidth map for the predetermined area, and (iii) establish an etch depth map for the predetermined area. The system may further be configured to, based on the initial device layer thickness map, the linewidth map and the etch depth map, calculate an optimal device layer thickness map and a corresponding thickness correction map for the predetermined substrate area taking into account photonic device design data. Still further, the system may be configured to perform a location specific corrective etch process in accordance with the thickness correction map.

In an example, the system may include a processor and data storage, each of which may take various forms. For instance, the processor could be one or more general purpose microprocessors and/or dedicated signal processors. Further, data storage could be volatile and/or non-volatile memory, such as flash memory. Still further, the data storage may comprise instructions executable by the processor to (i) establish an initial device layer thickness map for the predetermined area, (ii) establish a linewidth map for the predetermined area, (iii) establish an etch depth map for the predetermined area, (iv) based on the initial device layer thickness map, the linewidth map and the etch depth map, calculate an optimal device layer thickness map and a corresponding thickness correction map for the predetermined substrate area taking into account photonic device design data, and (v) initiate or perform a location specific corrective etch process in accordance with the thickness correction map. The system may comprise an etch apparatus configured to perform a location specific corrective etch process in accordance with the thickness correction map.

The foregoing description details certain embodiments of the disclosure. It will be appreciated, however, that no matter how detailed the foregoing appears in text, the disclosure may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

While the above detailed description has shown, described, and pointed out novel features of the disclosure as applied to various embodiments, it will be understood that various omissions, substitutions, and changes in the form and details of the device or process illustrated may be made by those skilled in the technology without departing from the spirit of the disclosure. For instance, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A method for improving the uniformity over a predetermined substrate area of a spectral response of photonic devices fabricated in a device layer of a Silicon-On-Insulator substrate, wherein the device layer of the Silicon-On-Insulator substrate is a silicon device layer on a silicon dioxide layer, the method comprising:

before fabrication of the photonic device structures in the device layer of the Silicon-On-Insulator substrate,
(i.) establishing an initial device layer thickness map for the predetermined area;

(ii) establishing an anticipated linewidth map for the predetermined area, wherein establishing the anticipated linewidth map comprises establishing, based at least on previously-collected process control data from optical lithography and from dry etching, an anticipated linewidth as a function of spatial wafer coordinates in the predetermined area;

(iii) establishing an anticipated etch depth map for the predetermined area, wherein establishing the anticipated etch depth map comprises establishing, based at least on previously-collected process control data from optical lithography and from dry etching, an anticipated etch depth as a function of spatial wafer coordinates in the predetermined area;

(iv) based at least on the initial device layer thickness map, the anticipated linewidth map and the anticipated etch depth map, calculating (i) an optimal device layer thickness map for matching a predetermined spectral response of a photonic device and (ii) a corresponding thickness correction map for the predetermined substrate area taking into account photonic device design data; and (v) performing a location specific corrective etch process in accordance with the thickness correction map.

2. The method of claim 1, wherein establishing the initial device layer thickness map comprises measuring the initial thickness of the device layer over the predetermined substrate area as a function of x and y, where x and y are spatial wafer coordinates.

3. The method of claim 2, wherein measuring the initial thickness of the device layer comprises measuring by spectroscopic ellipsometry.

4. The method of claim 2, wherein measuring the initial thickness of the device layer is performed with an accuracy better than 1 nanometer (nm).

5. The method of claim 1, wherein calculating the optimal device layer thickness map comprises calculating, as a function of spatial wafer coordinates, an optimal device layer thickness needed for matching the predetermined spectral response of the photonic device.

6. The method of claim 1, wherein determining the thickness correction map comprises calculating a difference between the optimal device layer thickness and the initial device layer thickness as a function of spatial wafer coordinates, wherein the difference corresponds to the thickness correction to be performed by the location specific corrective etch process.

7. The method of claim 1, wherein the location specific corrective etch process is a Gas Cluster Ion Beam process.

8. The method of claim 1, further comprising performing a second location specific corrective etch process after fabrication of the photonic device structures in the device layer of the Silicon-On-Insulator substrate.

* * * * *